(12) United States Patent
Richey, II et al.

(10) Patent No.: US 10,300,427 B2
(45) Date of Patent: May 28, 2019

(54) SYSTEM AND METHOD FOR CONCENTRATING GAS

(71) Applicant: Invacare Corporation, Elyria, OH (US)

(72) Inventors: Joseph B. Richey, II, Chagrin Falls, OH (US); William J. Daniels, Wadsworth, OH (US)

(73) Assignee: Invacare Corporation, Elyria, OH (US)

( * ) Notice: Subject to any disclaimer, the term of this patent is extended or adjusted under 35 U.S.C. 154(b) by 75 days.

(21) Appl. No.: 15/640,680

(22) Filed: Jul. 3, 2017

(65) Prior Publication Data

US 2018/0078891 A1 Mar. 22, 2018

Related U.S. Application Data

(63) Continuation of application No. 14/852,721, filed on Sep. 14, 2015, now Pat. No. 9,694,311, which is a
(Continued)

(51) Int. Cl.
*B01D 53/047* (2006.01)
*A61M 16/10* (2006.01)
(Continued)

(52) U.S. Cl.
CPC ....... *B01D 53/0454* (2013.01); *A61M 16/101* (2014.02); *B01D 53/0446* (2013.01);
(Continued)

(58) Field of Classification Search
CPC .............. A61M 16/101; A61M 16/107; A61M 2016/102; C01B 13/0259; C01B 21/0466;
(Continued)

(56) References Cited

U.S. PATENT DOCUMENTS

| 4,127,395 A | 11/1978 | McKey et al. |
| 4,144,037 A | 3/1979 | Armond et al. |

(Continued)

FOREIGN PATENT DOCUMENTS

| CA | 2438457 | 2/2004 |
| CN | 87102164 | 11/1987 |

(Continued)

OTHER PUBLICATIONS

Office action from New Zealand Application No. 603120 dated Oct. 26, 2012.
(Continued)

*Primary Examiner* — Frank M Lawrence, Jr.
(74) *Attorney, Agent, or Firm* — Calfee, Halter & Griswold LLP

(57) ABSTRACT

Systems and methods for producing a product gas are provided. In one embodiment, a system includes at least one separation bed to separate adsorbable components from a gas source, a valving means to selectively direct gas from the gas source to the at least one separation bed, at least one sensing device associated with the at least one separation bed to sense the progress of an adsorption zone within the separation bed, and a controller. The controller includes logic to read the output of the at least one sensing device and control the gas separation process based on the progress of the adsorption zone.

20 Claims, 13 Drawing Sheets

Related U.S. Application Data continuation of application No. 13/790,826, filed on Mar. 8, 2013, now Pat. No. 9,132,377.

(60) Provisional application No. 61/608,874, filed on Mar. 9, 2012.

(51) Int. Cl.
| | | |
|---|---|---|
| *B01D 53/04* | (2006.01) | |
| *C01B 13/02* | (2006.01) | |
| *C01B 21/04* | (2006.01) | |
| *B01D 53/053* | (2006.01) | |

(52) U.S. Cl.
CPC ....... *B01D 53/0462* (2013.01); *B01D 53/053* (2013.01); *C01B 13/0259* (2013.01); *C01B 21/0466* (2013.01); *A61M 16/107* (2014.02); *A61M 2016/102* (2013.01); *B01D 2253/108* (2013.01); *B01D 2256/12* (2013.01); *B01D 2257/102* (2013.01); *B01D 2257/502* (2013.01); *B01D 2257/504* (2013.01); *B01D 2257/80* (2013.01); *B01D 2258/06* (2013.01); *B01D 2259/402* (2013.01); *B01D 2259/40003* (2013.01); *B01D 2259/40009* (2013.01); *B01D 2259/4533* (2013.01); *Y02C 10/08* (2013.01); *Y02P 20/152* (2015.11)

(58) Field of Classification Search
CPC ............ B01D 53/0446; B01D 53/0454; B01D 53/0461; B01D 53/053; B01D 2253/108; B01D 2256/12; B01D 2257/102; B01D 2257/502; B01D 2257/504; B01D 2257/80; B01D 2258/06; B01D 2259/40003; B01D 2259/40009; B01D 2259/402; B01D 2259/4533; Y02C 10/08; Y02P 20/152
USPC ............ 95/1, 8, 11, 14, 19, 22, 23, 95, 130; 96/109–116, 121; 128/204.18, 205.27, 128/205.24
See application file for complete search history.

(56) References Cited

U.S. PATENT DOCUMENTS

| | | |
|---|---|---|
| 4,247,311 A | 1/1981 | Seibert |
| 4,449,990 A | 5/1984 | Tedford |
| 4,561,287 A | 12/1985 | Rowland |
| 4,575,042 A | 9/1986 | Grimland |
| 4,648,888 A | 3/1987 | Rowland |
| 4,826,510 A | 5/1989 | McCombs |
| 4,832,711 A | 5/1989 | Christel, Jr. et al. |
| 4,932,402 A | 6/1990 | Snook et al. |
| 4,971,609 A | 11/1990 | Pawlos |
| 5,099,837 A | 3/1992 | Russel et al. |
| 5,258,056 A | 11/1993 | Shirley et al. |
| 5,474,595 A | 12/1995 | McCombs |
| 5,593,478 A | 1/1997 | Hill et al. |
| 5,626,131 A | 5/1997 | Chua et al. |
| 5,720,276 A | 2/1998 | Kobatake et al. |
| 5,785,681 A | 7/1998 | Indravudh |
| 5,906,672 A | 5/1999 | Michaels et al. |
| 5,917,135 A | 6/1999 | Michaels et al. |
| 5,988,165 A | 11/1999 | Richey, II et al. |
| 6,051,051 A | 4/2000 | Hees et al. |
| 6,106,245 A | 8/2000 | Cabuz |
| 6,427,690 B1 | 8/2002 | McCombs et al. |
| 6,517,610 B1 | 2/2003 | De La Houssaye |
| 6,520,176 B1 | 2/2003 | Dubois et al. |
| 6,561,187 B2 | 5/2003 | Schmidt et al. |
| 6,629,525 B2 | 10/2003 | Hill et al. |
| 6,651,658 B1 | 11/2003 | Hill et al. |
| 6,691,702 B2 | 2/2004 | Appel et al. |
| 6,764,534 B2 | 7/2004 | McCombs et al. |
| 6,837,244 B2 | 1/2005 | Yagi et al. |
| 6,878,186 B2 | 4/2005 | Neary |
| 6,949,133 B2 | 9/2005 | McCombs et al. |
| 6,962,654 B2 | 11/2005 | Arnaud |
| 7,294,170 B2 | 11/2007 | Richey, II et al. |
| 7,306,657 B2 | 12/2007 | Yagi et al. |
| 7,329,304 B2 | 2/2008 | Bliss et al. |
| 7,393,382 B2 | 7/2008 | Givens |
| 7,445,663 B1 | 11/2008 | Hunter et al. |
| 7,455,717 B2 | 11/2008 | Sprinkle |
| 7,604,005 B2 | 10/2009 | Jagger et al. |
| 7,686,870 B1 | 3/2010 | Deane et al. |
| 7,722,700 B2 | 5/2010 | Sprinkle |
| 7,766,010 B2 | 8/2010 | Jagger et al. |
| 7,866,315 B2 | 1/2011 | Jagger et al. |
| 7,875,105 B2 | 1/2011 | Chambers et al. |
| 8,062,003 B2 | 11/2011 | Goertzen et al. |
| 8,070,853 B2 | 12/2011 | Sprinkle |
| 8,262,771 B2 | 9/2012 | Seki et al. |
| 2002/0053286 A1 | 5/2002 | Czabala |
| 2003/0180164 A1 | 9/2003 | Bunner et al. |
| 2003/0215342 A1 | 11/2003 | Higashino |
| 2003/0231967 A1 | 12/2003 | Najafi et al. |
| 2004/0079359 A1 | 4/2004 | Aylsworth et al. |
| 2006/0005482 A1 | 1/2006 | Rashad |
| 2006/0086251 A1 | 4/2006 | Sprinkle |
| 2006/0174872 A1 | 8/2006 | Jagger |
| 2006/0219245 A1 | 10/2006 | Holder |
| 2006/0230929 A1 | 10/2006 | Bliss et al. |
| 2008/0066616 A1 | 3/2008 | Sprinkle |
| 2008/0257145 A1 | 10/2008 | Sprinkle |
| 2009/0065526 A1 | 3/2009 | Sprinkle |
| 2009/0211448 A1 | 8/2009 | McClain |
| 2010/0071698 A1 | 3/2010 | Kiritake |
| 2010/0095841 A1 | 4/2010 | Naheiri |
| 2010/0114218 A1 | 5/2010 | Heath |
| 2010/0242734 A1 | 9/2010 | Maeda et al. |
| 2011/0017216 A1 | 1/2011 | Van Brunt et al. |
| 2011/0315140 A1 | 12/2011 | Shuman |
| 2013/0233168 A1 | 9/2013 | Richey, II |

FOREIGN PATENT DOCUMENTS

| | | |
|---|---|---|
| CN | 1697681 | 11/2005 |
| CN | 1697682 | 11/2005 |
| CN | 101687134 A | 3/2010 |
| DE | 29605889 | 6/1996 |
| DE | 102007 021564 | 11/2008 |
| EP | 420620 | 4/1991 |
| EP | 1661596 | 5/2006 |
| GB | 1270296 | 4/1972 |
| WO | 98/56488 | 12/1998 |
| WO | 98/57165 | 12/1998 |
| WO | 06/92635 A1 | 9/2006 |
| WO | 08/036159 | 3/2008 |
| WO | 08/131338 | 10/2008 |
| WO | 13/134645 | 9/2013 |

OTHER PUBLICATIONS

Response from New Zealand Application No. 603120 dated Dec. 23, 2013.
First Examination Report from New Zealand Application No. 619,142 dated Jan. 29, 2014.
Examination Report from New Zealand Application No. 619,142 dated May 6, 2015.
First Examination Report from New Zealand Application No. 631,712 dated Apr. 28, 2015.
First Examination Report from New Zealand Application No. 706,769 dated May 6, 2015.
Office Action from Chinese Application No. 200780034658.2 dated Nov. 14, 2011.
Response to Office Action from Chinese Application No. 200780034658.2 dated May 4, 2012.
Office action from Chinese Application No. 200780034658.2 dated Aug. 1, 2012.

(56) References Cited

OTHER PUBLICATIONS

Response to Second Office action from Chinese Application No. 200780034658.2 dated Dec. 17, 2012.
Third Office Action from Chinese Application No. 200780034658.2 dated Jan. 21, 2013.
Response to Third Office Action from Chinese Application No. 200780034658.2 dated Jun. 5, 2013.
Office action from Chinese Application No. 200780034658.2 dated Jun. 19, 2013.
Response from Chinese Application No. 200780034658.2 dated Nov. 4, 2013.
Office Action from Chinese Application No. 200880021148.6 dated Nov. 1, 2011.
Response to Office Action from Chinese Application No. 200880021148.6 dated May 13, 2012.
Second Office Action from Chinese Application No. 200880021148.6 dated Oct. 25, 2012.
Response from Chinese Application No. 200880021148.6 dated Mar. 8, 2013.
Third Office Action from Chinese Application No. 200880021148.6 dated May 2, 2013.
Response from Chinese Application No. 200880021148.6 dated Jul. 17, 2013.
First Office Action from Chinese Application No. 201310563818.X dated Feb. 28, 2015.
Search Report from Chinese Application No. 201310563818.X dated Feb. 10, 2015.
First Office Action from Chinese Application No. 201480013306.9 dated Jul. 13, 2016.
Second Office Action from Chinese Application No. 201480013306.9 dated Mar. 8, 2017.
First Office Action in Colombian Application No. 09028163 dated Aug. 22, 2012.
Response from Colombian Application No. 09028163 dated Nov. 6, 2012.
First Examination Report from New Zealand Application No. 709919 dated Feb. 3, 2017.
First Examination report from New Zealand Application No. 722551 dated Aug. 4, 2016.
Partial International Search Report from PCT/US13/46086 dated Sep. 23, 2013.
International Search Report from PCT/US13/46086 dated Dec. 12, 2013.
International Preliminary Report on Patentability from PCT/US13/46086 dated Dec. 23, 2014.
International Search Report and Written Opinion from PCT/US14/10409 dated Jun. 12, 2014.
Notice of Allowance from U.S. Appl. No. 13/790,826 dated Jan. 22, 2015.
Office action from U.S. Appl. No. 12/106,861 dated Dec. 7, 2010.
International Search Report and Written Opinion from PCT/US07/18468 dated Feb. 11, 2008.
International Search Report and Written Opinion from PCT/US08/61022 dated Jul. 18, 2008.
International Search Report and Written Opinion from PCT/US13/029885 dated May 31, 2013.
Invacare Corporation, Oxygen Products Brochure, Form No. 05-054, 20 pages, copyright 2005.
Invacare Corporation, Oxygen Products Brochure, Form. No. 05-054, 16 pgs., copyright 2008.
Invacare Corp., XP02 Portable Concentrator, Invacare Product Catalog, www.invacare.com/cgi-bin/imhqprd/inv_catalog/prod_cat_detail.jsp?s=0 & prodID=XPO100 & catOID=-536885301, printed Mar. 17, 2008, 1 pg.
Office action from U.S. Appl. No. 11/258,480 dated Feb. 12, 2008.
Response to Office action from U.S. Appl. No. 11/258,480 dated May 9, 2008.
Notice of Allowance from U.S. Appl. No. 11/258,480 dated Jul. 21, 2008.
Office action from U.S. Appl. No. 11/522,683 dated Jun. 8, 2009.
Response to Office action from U.S. Appl. No. 11/522,683 dated Dec. 8, 2009.
Notice of Allowance from U.S. Appl. No. 11/522,683 dated Dec. 30, 2009.
Office action from U.S. Appl. No. 12/106,861 dated Jul. 21, 2010.
Response from U.S. Appl. No. 12/106,861 dated Oct. 21, 2010.
Response from U.S. Appl. No. 12/106,861 dated Apr. 6, 2011.
Office Action from U.S. Appl. No. 12/106,861 dated Jun. 14, 2012.
Amendment from U.S. Appl. No. 12/106,861 dated Oct. 15, 2012.
Final Office Action from U.S. Appl. No. 12/106,861 dated Oct. 23, 2012.
Amendment with RCE from U.S. Appl. No. 12/106,861 dated Jan. 23, 2013.
Notice of Allowance US U.S. Appl. No. 12/106,861 dated Jun. 12, 2013.
Office action from U.S. Appl. No. 12/274,026 dated Nov. 8, 2010.
Amendment with Terminal Disclaimer from U.S. Appl. No. 12/274,026 dated Mar. 8, 2011.
Notice of Allowance from U.S. Appl. No. 12/274,026 dated May 11, 2011.
Notice of Allowance from U.S. Appl. No. 12/274,026 dated Sep. 28, 2011.
Office Action from U.S. Appl. No. 13/790,826 dated Sep. 9, 2014.
Response to Office Action from U.S. Appl. No. 13/790,826 dated Dec. 9, 2014.
Notice of Allowance from U.S. Appl. No. 13/790,826 dated May 11, 2015.
Office Action from U.S. Appl. No. 13/839,954 dated Oct. 9, 2014.
Response to Office Action from U.S. Appl. No. 13/839,954 dated Jan. 9, 2015.
Notice of Allowance from U.S. Appl. No. 13/839,954 dated Feb. 20, 2015.
Office Action from U.S. Appl. No. 13/790,473 dated Sep. 9, 2014.
Response to Office Action from U.S. Appl. No. 13/790,473 dated Dec. 9, 2014.
Office Action from U.S. Appl. No. 13/790,312 dated Mar. 5, 2015.
Response to Office Action from U.S. Appl. No. 13/790,312 dated Aug. 4, 2015.
Notice of Allowance from U.S. Appl. No. 13/790,312 dated Aug. 20, 2015.
Notice of Allowance from U.S. Appl. No. 13/790,473 dated Jan. 12, 2015.
Notice of Allowance from U.S. Appl. No. 13/790,473 dated Apr. 21, 2015.
Notice of Allowance from U.S. Appl. No. 14/202,536 dated Mar. 3, 2016.
Office Action from U.S. Appl. No. 14/852,721 dated Oct. 18, 2016.
Response to Office Action from U.S. Appl. No. 14/852,721 dated Jan. 18, 2017.
Notice of Allowance from U.S. Appl. No. 14/852,721 dated Mar. 1, 2017.
Office Action from U.S. Appl. No. 15/193,521 dated Sep. 13, 2017.
Response to Office Action from U.S. Appl. No. 15/193,521 dated Jan. 12, 2018.
Notice of Allowance from U.S. Appl. No. 15/193,521 dated Mar. 14, 2018.
Examination Report from AU Application No. 2007297814 dated Feb. 4, 2010.
Response from Australian Application No. 2007297814 dated Apr. 4, 2011.
Office action from Australian Application No. 2008242596 dated Jul. 14, 2010.
Response from Australian Application No. 2008242596 dated Sep. 26, 2011.
Further Examination Report from Australian Application No. 2008242596 dated Oct. 7, 2011.
Response to Examiner's Second Report from Australian Application No. 2008242596 dated Feb. 8, 2012.
First Office Action in AU Patent Application No. 2012203342 dated Dec. 21, 2012.
First Examination Report from Australian Application No. 2014203773 dated Aug. 7, 2015.

(56) References Cited

OTHER PUBLICATIONS

First Examination Report from Australian Application No. 2013229908 dated Mar. 24, 2017.
Office action from Canadian Application No. 2,663,902 dated Oct. 20, 2010.
Response to Office Action from Canadian Application No. 2,663,902 dated Apr. 20, 2011.
Office action from Canadian Application No. 2,684,871 dated May 31, 2011.
Response to Office Action from Canadian Application No. 2,684,871 dated Nov. 30, 2011.
First Office Action in Canadian Application No. 2,793,228 dated Jan. 8, 2013.
Response from Canadian Application No. 2,793,228 dated Jun. 17, 2013.
Second Office Action from Canadian Application No. 2,793,228 dated Jul. 29, 2013.
Response to Office Action from Canadian Application No. 2,793,228 dated Jan. 29, 2014.
Office Action from Canadian Application No. 2,871,228 dated Nov. 9, 2015.
Response to Office Action from Canadian Application No. 2,871,228 dated May 3, 2015.
Office Action from Canadian Application No. 2,871,228 dated May 11, 2016.
Office Action from Canadian Application No. 2,871,228 dated Nov. 28, 2016.
First Office Action from Chinese Application No. 201380024109.2 dated Aug. 7, 2015.
Response to Office Action from Chinese Application No. 201380024109.2 dated Feb. 22, 2016.
Office Action from Chinese Application No. 201380024109.2 dated Jun. 13, 2016.
Communication from EP Application No. 07837126.7 dated Sep. 3, 2010.
Response from EP Application No. 07837126.7 dated Mar. 14, 2011.
Exam Report from EP Application No. 07837126.7 dated Sep. 27, 2011.
Response from EP Application No. 07837126.7 dated Mar. 16, 2012.
Notice of Grant of EP Application No. 07837126.7 dated Jul. 8, 2013.
Search Report from EP Application No. 08746446.7 dated Aug. 2, 2011.
Response from EP Application No. 08746446.7 dated Feb. 3, 2012.
Office Action from EP Application No. 08746446.7 dated Jun. 27, 2012.
Response to Communication from EP Application No. 08746446.7 dated Dec. 27, 2012.
Response to OA requesting claims in EP Application No. 12184137.3 dated Dec. 4, 2012.
Extended EP Search Report for EP Application No. 12184137.3 dated Feb. 14, 2013.
Response from European Application No. 12184137.3 dated Aug. 27, 2013.
Office action from European Application No. 12184137.3 dated Oct. 1, 2013.
Response from European Application No. 12184137.3 dated Apr. 11, 2014.
Summons to Attend Oral Hearing from European Application No. 12184137.3 dated Apr. 8, 2015.
Communication to Rules 161(1) and 162 EPC from European Application No. 137107464.5 dated Nov. 7, 2014.
Communication pursuant to Article 94(3) EPC from European Application No. 13710764.5 dated Apr. 13, 2016.
Communication Pursuant to Article 94(3) EPC from European Application No. 13710764.5 dated Jan. 3, 2017.
Communication Pursuant to Article 94(3) EPC from European Application No. 14703185.0 dated Feb. 22, 2017.
Search Report from European Application No. 15170789.0 dated Dec. 2, 2015.
Rule 69 EPC Communication from European Application No. 15170789.0 dated Feb. 1, 2016.
Communication Pursuant to Article 94(3) EPC dated from European Patent Application No. 15170789.0 dated Aug. 3, 2017.
Examination Report from New Zealand Application No. 575,059 dated Dec. 15, 2010.
Response to New Zealand Application No. 575,059 dated May 8, 2012.
Office Action from New Zealand Application No. 575,059 dated May 22, 2012.
Response to Office Action from New Zealand Application No. 575,059 dated Jun. 28, 2012.
First Examination Report from New Zealand Application No. 580,515 dated Mar. 23, 2011.
Examination Report from New Zealand Application No. 580,515 dated Aug. 14, 2012.
Response to First Examination Report from New Zealand Application No. 580,515 dated Jul. 23, 2012.
Response to Second Examination Report from New Zealand Application No. 580,515 dated Oct. 18, 2012.
Third Examination Report from New Zealand Application No. 580,515 dated Nov. 9, 2012.
Response to Third Examination Report from New Zealand Application No. 580,515 dated Nov. 15, 2012.
Examination Report from Australian Application No. 2014205643 dated Jun. 29, 2018.

SYSTEM AND METHOD FOR CONCENTRATING GAS

CROSS REFERENCE TO RELATED APPLICATIONS

This application claims priority to, and the benefits of, U.S. application Ser. No. 14/852,721, filed on Sep. 14, 2015, which is a continuation of U.S. application Ser. No. 13/790, 826, filed on Mar. 8, 2013, which claims the benefit of U.S. provisional application Ser. No. 61/608,874, filed on Mar. 9, 2012, which is incorporated by reference herein in full.

BACKGROUND

Various applications exist for the separation of gaseous mixtures. For example, the separation of nitrogen from atmospheric air can provide a highly concentrated source of oxygen. These various applications include the provision of elevated concentrations of oxygen for medical patients and flight personnel. Hence, it is desirable to provide systems that separate gaseous mixtures to provide a concentrated product gas, such as a breathing gas with a concentration of oxygen.

Several existing product gas or oxygen concentrating systems and methods, for example, are disclosed in U.S. Pat. Nos. 4,449,990, 5,906,672, 5,917,135, 5,988,165, 7,294, 170, 7,455,717, 7,722,700, 7,875,105, 8,062,003, 8,070,853 and U.S. patent application Ser. Nos. 12/106,861, 61/661, 260, 61/750,517, 13/790,312, and 13/790,473, which are commonly assigned to Invacare Corporation of Elyria, Ohio and fully incorporated herein by reference.

SUMMARY

In one embodiment, a system for producing a product gas is provided. The system includes, for example, at least one separation bed to separate adsorbable components from a gas source, a valving means to selectively direct gas from the gas source to the at least one separation bed, at least one sensing device associated with the at least one separation bed to sense the progress of an adsorption zone within the separation bed, and a controller. The controller includes logic to read the output of the at least one sensing device and control the gas separation process based on the progress of the adsorption zone.

The descriptions of the invention do not limit the words used in the claims in any way or the scope of the claims or invention. The words used in the claims have all of their full ordinary meanings.

BRIEF DESCRIPTION OF THE DRAWINGS

In the accompanying drawings, which are incorporated in and constitute a part of the specification, embodiments of the invention are illustrated, which, together with a general description of the invention given above, and the detailed description given below, serve to exemplify embodiments of this invention.

DESCRIPTION

As described herein, when one or more components are described or shown as being connected, joined, affixed, coupled, attached, or otherwise interconnected, such interconnection may be direct as between the components or may be in direct such as through the use of one or more intermediary components. Also as described herein, reference to a member, component, or portion shall not be limited to a single structural member, component, element, or portion but can include an assembly of components, members, elements, or portions. Furthermore, any one or more components may be integrated into common housings, assemblies or other components.

Figure 1:
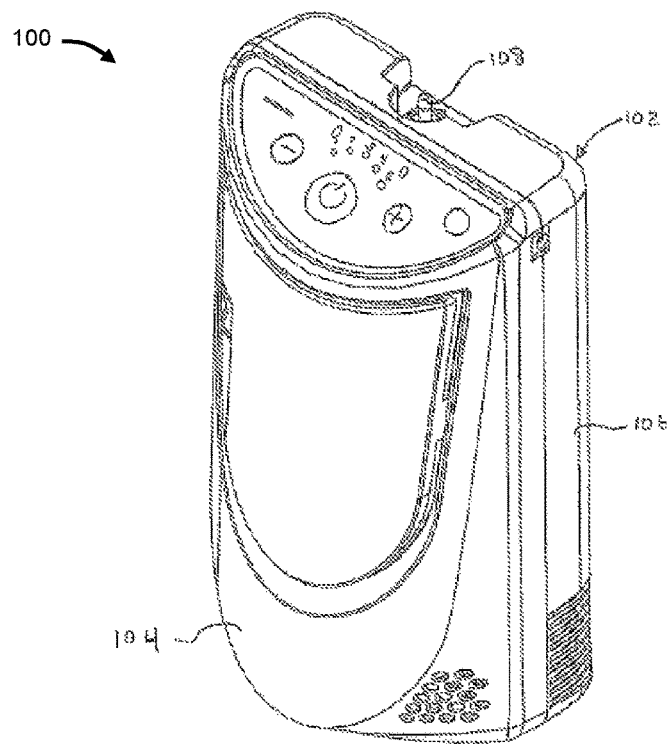
FIG. 1 illustrates an embodiment of a gas concentrating system.

Illustrated in FIG. 1 is one embodiment of an exemplary gas concentrating system 100. System 100 may be an oxygen concentrating system. The system may be stationary such as, for example, for use in a hospital or a patient's home. The system can also be ambulatory or mobile such as, for example, for use by a patient when they are away from home. The system can be configured in a manner so as to allow the patient to carry system such as, for example, through an over the shoulder strap or through an arrangement whereby the system includes a handle and wheels. Other mobility configurations are also included.

System 100 includes a housing 102 having a front portion 104 and a rear portion 106. Front and rear portions 104 and 106 include a plurality of openings for the intake and discharge of various gases such as, for example, the intake of room air and the discharge of nitrogen and other gases in the case of oxygen concentration. System 100 generally intakes room air, which is mostly comprised of nitrogen and oxygen, and separates the nitrogen from the oxygen. The oxygen may be stored in one or more storage tanks and the nitrogen is discharged back into the room air. For example, the oxygen gas may be discharged through port 108 to a user, such as a patient, through tubing and nasal cannula. In another embodiment, the oxygen gas may be discharged through a supplemental port to an oxygen cylinder filling device, such as HOMEFILL® that is manufactured by Invacare Corp. of Elyria, Ohio, USA.

Figure 2:
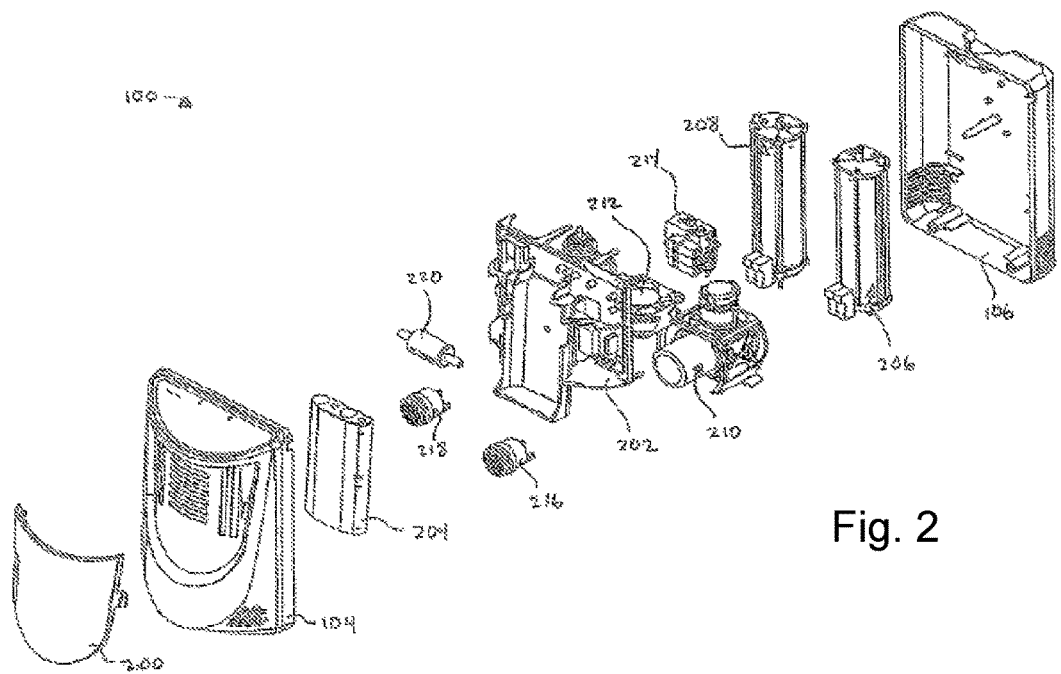
FIG. 2 illustrates an exploded view of a gas concentrating system.

FIG. 2 is an exploded perspective of the exemplary gas concentrating system 100 of FIG. 1. System 100 further includes a central frame 202 having a circuit board and other components connected thereto. These components include a battery pack 204, sieve/separation bed and product tank assemblies 206 and 208, cooling fan 212, and valve assembly 214. While these components are described as being connected to central frame 202 that need not be the case. One or more of these components may be connected to housing portions 104 or 106. Other components are also housed within oxygen system 100 including, for example, compressor assembly 210, which may include a pressure and/or a vacuum pump, sound attenuators or mufflers 216 and 218 and inlet filter 220. Exemplary compressors and pumps include, for example, WOB-L Piston Air Compressors and Vacuum Pumps, including models 8003, 8005, 8006, and 8009. These include single head, dual head, and speed adjustable pumps with various specifications. In other embodiments, more or less components can be part of system 100. For example, additional separation beds and product tanks, compressors, pumps, vacuums, filters, flow paths, sensors, etc. can be used. System 100 may also include more than one valve assembly 214.

Figure 3A:
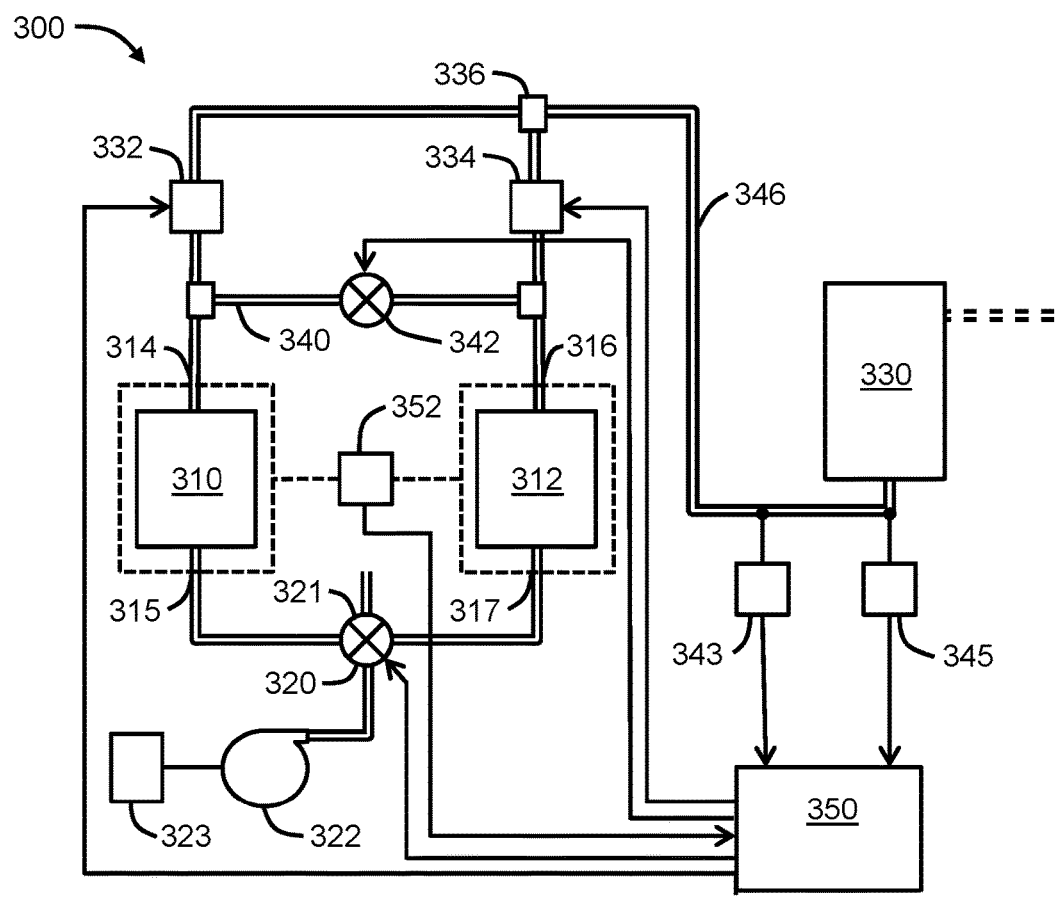
FIGS. 3A and 3B illustrate in schematic form two embodiments of gas concentrating systems with sensing devices associated with separation beds.

With reference to FIG. 3A, one exemplary embodiment of a schematic diagram of a gas concentrating system 300 is shown. The exemplary system 300 utilizes a pressure swing adsorption (PSA) process and includes at least two separation beds 310, 312 that contain separation material, such as, for example, a physical separation medium or material. The separation material selectively adsorbs one or more adsorbable components and passes one or more nonadsorbable components of a gaseous mixture to a separation bed outlet 314, 316. Generally, the physical separation material is a molecular sieve with pores of uniform size and essentially the same molecular dimensions. These pores selectively adsorb molecules in accordance with molecular shape, polarity, degree of saturation, and the like. In one embodiment, the physical separation medium is an aluminasilicate composition with 4 to 5 .ANG. (Angstrom) pores. More specifically, the molecular sieve is a sodium or calcium form of aluminasilicate, such as type 5A zeolite. Alternately, the aluminasilicate may have a higher silicon-to-aluminum ratio, larger pores, and an affinity for polar molecules, e.g., type 13× zeolite. The zeolite adsorbs nitrogen, carbon monoxide, carbon dioxide, water vapor, and other significant components of air. Other types of separation media may also be used. Also, more than two separation beds can be used.

A cross-over valving means 320, which can include various combinations and types of valves, such as, for example, a four-way valve 321, to selectively and cyclically connect the inlet end of one of the two separation beds 310, 312, in an alternating fashion, during a production/fill phase or cycle with a source of the gas mixture, for example, air under pressure supplied from a compressor or pressure source 322, while the other separation beds 310, 312 is vented to atmosphere during a purge phase or cycle. The cross-over valving means 320 selectively connects one of the separation beds 310, 312 in fluid communication with an air pump or compressor 322, which supplies air under about 15-30 pounds per square inch, during the fill phase. As used herein, "fluid communication" refers to means allowing flow of the appropriate gases. Another pressure or vacuum source (not shown) can also be used during the purge phase to enhance evacuation of the purging bed. The compressor 322 is connected to a drive motor 323.

A solenoid or other cross-over valve actuating means can selectively cause the cross-over valving means 320 to move alternately between first and second positions. In the first position, illustrated in FIG. 3, the first separation bed 310 is connected with the compressor 322 to cause nitrogen adsorption and oxygen enrichment in the product gas during a fill cycle, and the second separation bed 312 is vented to atmosphere to allow evacuation of the nitrogen during a purge cycle. In the second position, the first bed 310 is vented to atmosphere to allow evacuation of the nitrogen during a purge cycle and the second bed 312 is connected with the compressor 322 to cause nitrogen adsorption and oxygen concentration during a fill cycle. In some embodiment, venting during the purge cycle may be assisted by a vacuum.

As the gas mixture is introduced through a separation bed inlet 315, 317 to an adsorbed, gas-free or regenerated separation bed 310, 312, an adsorption zone of finite, relatively large size is formed. This adsorption zone is a region of the separation bed 310, 312 in which the full capacity of the adsorbent to hold the adsorbable components has not been reached. The composition of the gas in the voids of the zeolite varies from substantially pure primary-product gas at the separation bed outlet 314, 316, to the ambient gaseous mixture composition at the separation bed inlet 315, 317.

This adsorption zone moves from the separation bed inlet 315, 317 toward a separation bed outlet 314, 316 with a velocity significantly less than the superficial gas velocity in the separation bed 310, 312. When the adsorption zone reaches the separation bed outlet 314, 316, adsorbable components begin to flow through the separation bed outlet 314, 316 into the nonadsorbable primary product stream. This time is hereinafter referred to as the "breakthrough." For a given gaseous composition, the breakthrough is defined by the size and configuration of the bed container as well as the packing configuration of the molecular sieve and the flow rate and bed gas pressure. The bed container configuration is generally cylindrical, while the output volume rate can vary from about 0 to 6 liters per minute, and more specifically 3, 5, and 6 liters, respectively. The breakthrough is the time required for the diffusion reaction as the nitrogen saturates and is weakly bonded to the separation bed 310, 312 separation media.

Before breakthrough occurs, primary product-enriched bed gas in the zeolite voids varies from a higher primary product gas concentration at the separation bed outlet 314, 316 to a lower concentration at the separation bed inlet 315, 317. When breakthrough occurs, the primary product gas concentration at the separation bed outlet 314, 316 begins to shift to the lower concentration found at the separation bed inlet 315, 317, since the adsorption zone within the bed 310, 312 is nearly or completely filled. In the illustrated embodiment, the primary product-enriched bed gas is about 80 percent or more primary product at breakthrough. While adsorption is occurring in one separation bed 310, 312, the adsorbable components adsorbed by the separation media of the other separation bed 310, 312 are purged from the other separation bed 310, 312 because of the drop in pressure due to atmospheric venting and because of exposure to relatively pure product gas from the first separation bed 310, 312.

The control means 350 causes the cross-over valving means 320 to alternate between its first and second positions for the appropriate period during each cycle segment. A cycle segment can be either the product gas generation (e.g., fill) cycle or the purge cycle. The cycle duration is selected or determined such that each separation bed 310, 312 is connected with the source of air for a duration, which, for example, may be equal to or less than the breakthrough time.

The first separation bed 310 is connected with a reservoir or product tank 330 by way of a first valve 332, which may be, in this embodiment, a check valve or other unidirectional valving means. Product tank 330 may be a single tank or a plurality of individual tanks. The first valve 332 can permit the primary product gas from the first separation bed 310 to flow into the reservoir or product tank 330 when product gas pressure in the first separation bed 310 exceeds the pressure of product gas in the reservoir or product tank 330. The first valve 332 can prohibit the product gas from flowing from the reservoir or product tank 330 when the pressure in the first separation bed 310 is lower than in the reservoir or product tank 330. For example, the first valve 332 can impose a 1.5 psi bias such that flow is only permitted when the pressure in the first separation bed 310 exceeds the pressure in the reservoir or product tank 330 by 1.5 psi. The product gas concentration and pressure relative to the product tank 330 may also be read by sensors 343 and 345

The second separation bed 312 is connected with the reservoir or product tank 330 by way of a second valve 334, which may be, in this embodiment, a check valve or other unidirectional valving means. The second valve 334 again can provide for unidirectional flow of the primary product gas through product conduit 346 from the second separation bed 312 to the reservoir or product tank 330. In some embodiments, the system 300 may include another valve or union 336. In other embodiments, the separation beds 310 and 312 can be structurally integrated with the product tank 330, such as described in U.S. Patent Application Publication No. 2008/0257145, which is hereby fully incorporated by reference for this and other features.

In this embodiment, a pressure equalization flow path 340 extends between separation bed outlets 314 and 316 of the first and second separation beds 310 and 312. An equalization device or means 342, which can be a valve or similar flow control device, is either open or closed to selectively permit or prevent gas flow through the equalization flow path 340. An equalization valve 342 can be used to equalize the gas pressure and/or the gas concentration on either side of the equalization valve 342. A control means 350, which can be a microprocessor executing logic or software, cyclically can cause the cross-over valve actuating means (e.g., solenoids) 320 and the equalization valve 342 to be operated. The control means 350 can periodically and cyclically enable an equalization valve actuator which can also be a solenoid.

In this context, the gas mixture is supplied up to 32 pounds of pressure to the first separation bed 310, 312. Concurrently, the second separation bed 310, 312 (i.e., a "used" bed) is vented to atmosphere to cause purging of the nitrogen-enriched molecular sieves. Before the breakthrough time, the equalization valve 342 can be opened, allowing primary product-enriched gas from the filling first bed 310, 312 to flow into the evacuated second bed 310, 312. During the equalization period, one bed 310, 312 is or has been evacuated and the other bed 310, 312 has just reached the pressure set point which can drive flow between the beds 310, 312. The equalization flow is of high oxygen content so that the first product gas to pass into the product tank 330 from the newly filling bed 310, 312 is essentially product gas rather than vent gas.

After the primary product-enriched gas from the first bed 310, 312 is evacuated through the second bed 310, 312, the cross-over valving means 320 can be actuated to reverse its position. Actuating the cross-over valving means 320 discontinues supplying of the gaseous mixture to the first bed 310, 312 and commences evacuating it and concurrently discontinues evacuating the second bed 310, 312 and commences supplying it with the gaseous mixture.

Subsequent to the actuation of the cross-over valving means 320, the equalization valve 342 can remain open to continue allowing a purge supply of product-enriched gas to flow into the second bed 310, 312. This equalizes the pressure and/or concentration of gas which is supplied to the product tank 330 since the cycling is sequenced so that the product gas flows into the product tank 330 before breakthrough. Subsequently, the equalization valve 342 closes and terminates the flow of primary-product gas between the beds 310, 312.

In the second segment of the cycle, the pressure in the second bed 310, 312 increases, approaching the 32 psi gas mixture source pressure. Concurrently, the pressure in the first bed 310, 312 decreases approaching atmospheric pressure. Before the secondary product molecules have traversed the second bed 310, 312, the equalization valve 342 can be opened, allowing the primary product-enriched gas in the zeolite voids of the second bed 310, 312 to flow to the first bed 310, 312. While the primary product-enriched gas is flowing to the first bed 310, 312, the cross-over valving means 320 can be actuated. Actuating the cross-over valving means 320 discontinues the evacuation of the first bed 310, 312 and commences supplying the gaseous mixture and concurrently discontinues supplying the gaseous mixture to the second bed 310, 312 and commences evacuating it. Subsequent to actuating the cross-over valving means 320, the equalization valve 342 can be closed, terminating the pressure equalizing flow of the primary product-enriched gas between the beds 310, 312. The steps are cyclically repeated to provide continuing fractionating of the primary product gas from the source gas mixture.

In one embodiment, the mechanism triggering the cross-over valving means 320 and/or the equalization device 342 is the progress of the adsorption zone within each separation bed 310, 312, as sensed by sensing device 352. Based on the readings of sensing device 352 (e.g., oxygen concentration, nitrogen concentration, temperature, pressure, flow rate, etc.), the triggering mechanism can appropriately actuate cross-over valving means 320 and/or equalization device 342 when the adsorption zone reaches or nearly reaches the separation bed outlet 314, 316. The triggering mechanism may also be based on sampling over multiple fill cycles the average time it takes the adsorption zone to reach the separation bed outlet 314, 316. Further, the triggering mechanism can be based on a percentage of the average time that is less than the full time.

In yet other embodiments, the above triggering mechanism can further be combined with pressure, such as a pressure set point or set point range, associated with a bleed line from the product tank 330 as is used in a pressure-based control cycle, or it can be based strictly on a input gas residence time from the product-producing bed 310, 312, such as in a timing cycle-based control cycle. In accordance with another embodiment of the invention, the control cycle can utilize variable pressure in order to achieve an input gas residence time within a defined range based upon a projected breakthrough time.

In these embodiments, the progress of the adsorption zone towards the active separation bed outlet 314, 316 can be sensed through a variety of sensing devices or means 352 (e.g., oxygen concentration, nitrogen concentration, temperature, pressure, flow rate, etc.). For an oxygen producing separation bed 310, 312, when the adsorption zone reaches the separation bed outlet 314, 316, a significant drop in oxygen concentration (or a significant rise in nitrogen concentration) can be sensed. Similarly, when the adsorption zone reaches the separation bed outlet 314, 316, a rise in temperature and/or pressure can be sensed. This information is read by control means 350 through sensing device or means 352 and used to adjust the pneumatic components of the system such as, for example, the compressor 322, the cross-over valving means 320, the equalization device 342, etc., as described above. Other components can also be controlled including, for example, the speed of the compressor 322.

Figure 3B:
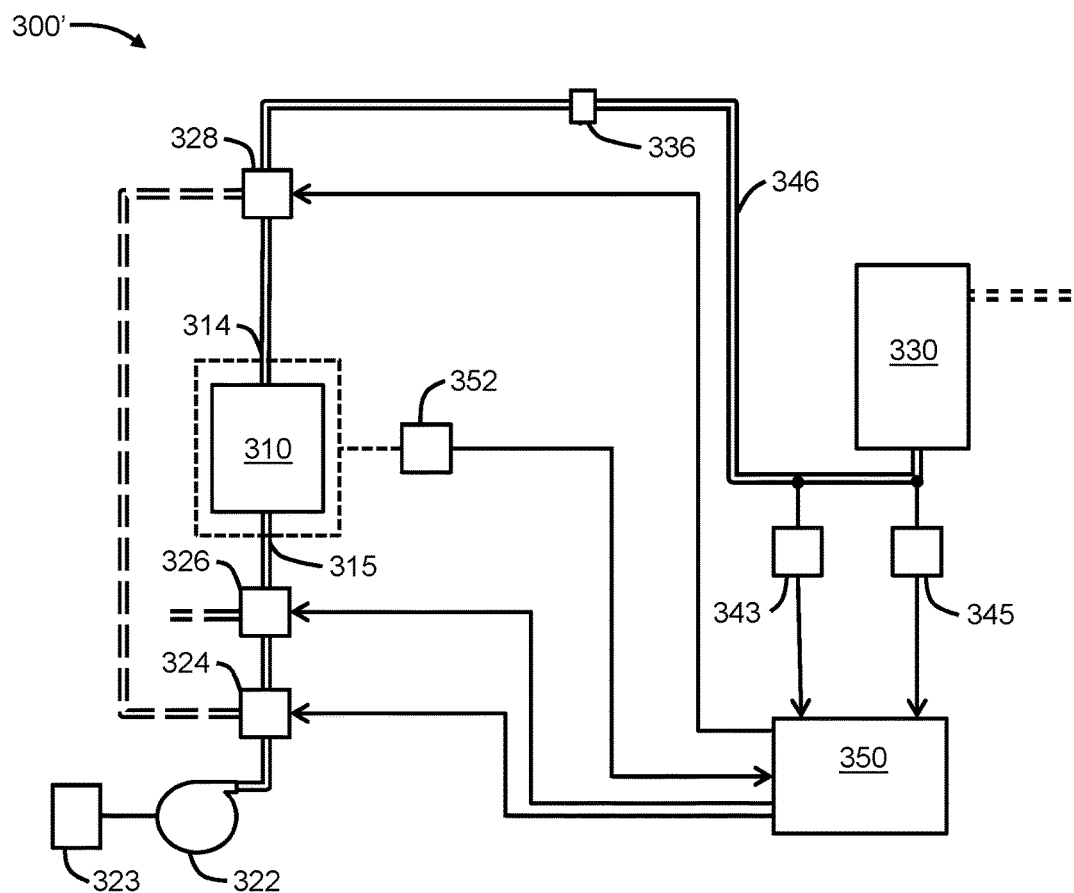

In another embodiment, as shown FIG. 3B, a schematic diagram of another gas concentrating system 300' is shown. The exemplary system 300' also utilizes a PSA process, but includes only separation bed 310. Operation of system 300' is similar to system 300, including alternating fill and purge cycles. However, system 300' includes valving means 324, 326, 328 to control the flow of gas through separation bed 310. During a fill cycle, the compressor 322 provides the source gas mixture to the separation bed 310 through valves 324 and 326 to the separation bed inlet 315. The concentrated oxygen product gas exits the separation bed 310 through the separation bed outlet 314 and flows to the product tank 330 through valves 328 and 336. Valve 336 may be a check valve.

As the separation bed 310 approaches breakthrough, as sensed by the sensing device or means 352, the control means 350 can change the position of valves 324, 326, and 328, such that valve 324 prevents the source gas mixture from entering the separation bed 310, valve 328 prevents the product gas from flowing to the product tank 330, and valve 326 connects the separation bed inlet 315 to the atmosphere to allow the separation bed to vent nitrogen as the pressure within the separation bed 310 equalizes. In another embodiment, as shown by the dashed flow path, valves 324 and 328 may also direct the gas mixture to the separation bed outlet 314 to assist in purging the nitrogen from the separation bed 310 during the purge cycle. Once separation bed 310 is purged, the valves 324, 326, 328 return to their fill cycle orientation to begin the next fill cycle.

It should be appreciated that the adsorption and desorption process is common to many types and configurations of gas concentrating systems, for example, as described in U.S. patent application Ser. No. 13/790,312, which is incorporated herein by reference in full. In addition, the feedback and control associated with the sensing devices (e.g., 352) described herein are applicable to these gas concentration systems.

Figure 4A:
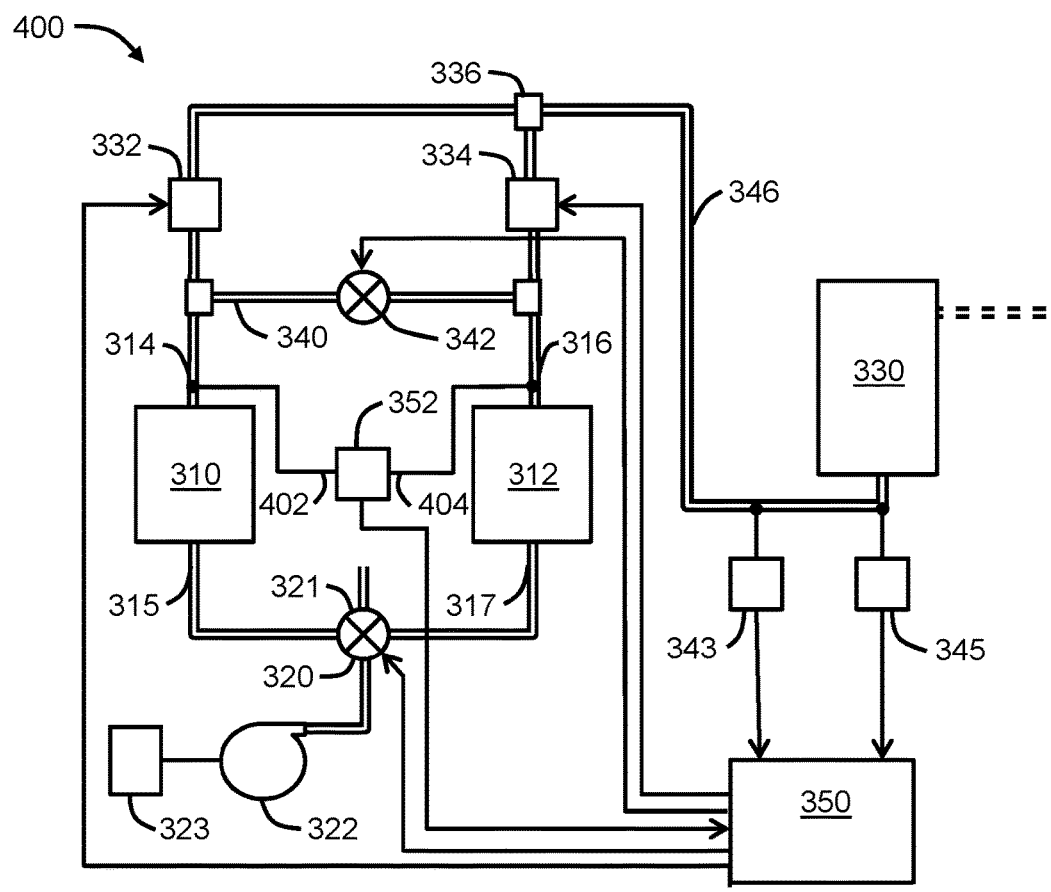
FIGS. 4A and 4B illustrate in schematic form two embodiments of gas concentrating systems with sensing devices associated with outlets of separation beds.

In one embodiment, as shown in FIG. 4A, an exemplary gas concentration system 400 includes sensing device or means 352 to sense when the adsorption zone reaches the separation bed outlet 314, 316. In one embodiment, the sensing device 352 is coupled to the separation bed outlets 314, 316 via lines 402, 404. Sensing device 352 is read by control means 350 to determine when that event occurs. For example, sensing device 352 can monitor separation bed 310 during its fill phase and then can monitor separation bed 312 during its fill phase. By monitoring the separation beds 310, 312 for when their respective adsorption zones reach their respective separation bed outlets 314, 316, or approximately reaches the separation bed outlets 314, 316, control means 350 can determine when subsequent events, such as, for example, the actuating of cross-over valving means 320, equalization valve 342, and the fill/purge cycle timing of the separation beds 310, 312 can occur. In this manner, the time that the equalization valve 342 remains open (in one direction) and, consequently, the amount of primary-product gas which is allowed to flow into the separation bed being evacuated can be controlled by the control means 350 to optimize (i.e., maximize) the oxygen outflow from the system 400.

In this embodiment, appropriate control valving may be used to control from which separation bed 310, 312 sensing device or means 352 is obtaining a reading. The control valving may be internal to sensing device or means 352 or may be in sensing paths 402 and 404.

While sensing device or means 352 can be any suitable sensor, in one embodiment it can be an oxygen concentration sensor or other type of oxygen sensor. Additionally, sensing device or means 352 can be a nitrogen sensor. Further still, sensing device or means 352 can be a temperature sensor that measures temperature differences as the adsorption zone travels through the separation bed. Any other type of sensor suitable for indicating the progress of the adsorption zone within a separation bed 310, 312 may be utilized. Moreover, in other embodiments, a plurality of sensors and sensor types can be used.

Still referring to FIG. 4A, the product gas concentration and pressure relative to the product tank 330 may be read by sensors 343 and 345. In one embodiment, an oxygen sensor 343 registers the oxygen concentration of the product gas and can be located in or proximate to the product tank 330. Sensor 343 can communicate a sensed value to the microprocessor (i.e., control means) 350. Similarly, pressure sensor 345 can register the pressure in the product tank 330 and can communicate the same to the microprocessor 350.

Figure 4B:
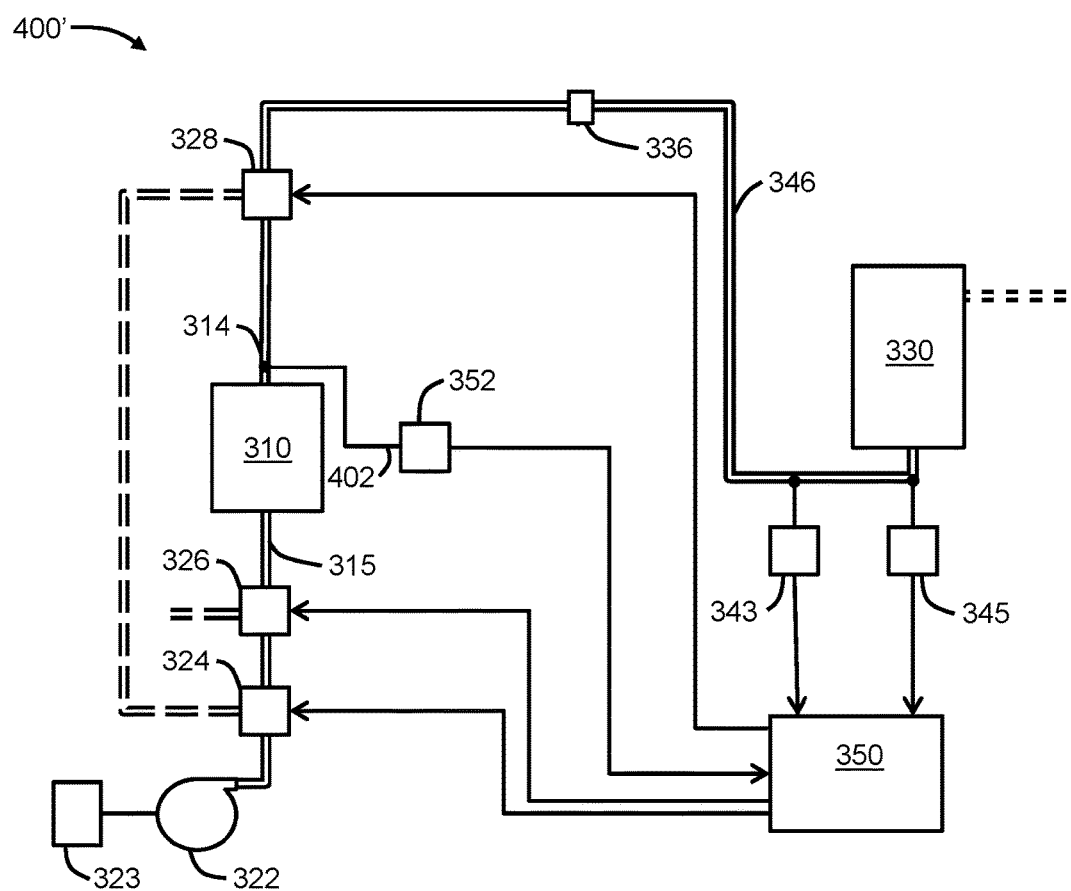

Similarly, referring to FIG. 4B, an exemplary gas concentration system 400' includes sensing device or means 352 to sense when the adsorption zone reaches the separation bed outlet 314 of a single separation bed 310 embodiment. In system 400', by monitoring the separation bed 310 for when the adsorption zone reaches the separation bed outlet 314, or approximately reaches the separation bed outlet 314, control means 350 can determine when subsequent events, such as, for example, the actuating of valving means 324, 326, 328, and the fill/purge cycle timing of the separation bed 310 can occur. In this manner, the control means 350 can optimize (i.e., maximize) the oxygen outflow from the system 400'.

Figure 5A:
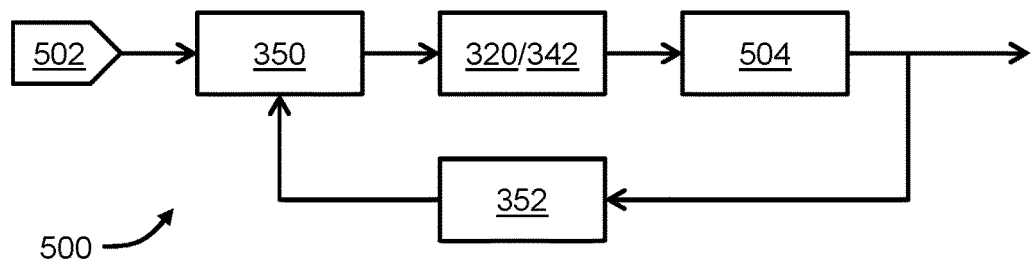
FIGS. 5A and 5B illustrate two embodiments of control diagrams for adjusting parameters associated with gas concentrating systems.

Referring to FIG. 5A, one exemplary embodiment of a control diagram 500 for a gas concentrating system, such as, for example, system 400, is illustrated. Control diagram 500 includes an initial set of control parameters 502 for controlling the pneumatic components of the system, control means 350, cross-over valving means 320 and/or equalization device 342, sensing device or means 352, and the remaining gas concentrating system components 504 (e.g., system 400 less components 320, 342, 350, and 352). The initial set of control parameters 502 are read or input into control means 350. Control means 350 uses this initial parameter set to define the initial timing of the cross-over valving means 320 and/or equalization device 342 (i.e., the equalization time between the separation beds). Control means 350 also uses this initial parameter set 502 to define the timing of other components in block 504 (including the initial timing of the cross-over valving means 320 or equalization device 342 if not already). Sensing device or means 352 senses the progress of the adsorption zone in the separation beds 310, 312 (as represented by block 404) and communicates that information or data to control means 350. Control means 350 then uses the information from sensing device or means 352 to adjust the control parameters used by control means 350 in operating the gas concentrating system.

In one example, initial control parameters 502 include the timing sequence of equalization device 342. The control means 350 uses those parameters to initially control when and for how long equalization device 342 allows product gas to flow from one separation bed 310, 312 to another bed 310, 312, as described above. After one or more fill/purge cycles, control means 350 reads the data from sensing device or means 352, which may be an oxygen concentration sensor associated with the separation bed outlet 314, 316, and uses that data to adjust the timing and/order duration of the opening and closing of equalization device 342 during a fill/purge cycle. Control means 350 can use that data from sensing device or means 352 upon every fill/purge cycle or intervals defined by one or more fill/purge cycles, time, or any other sequence.

Figure 5B:
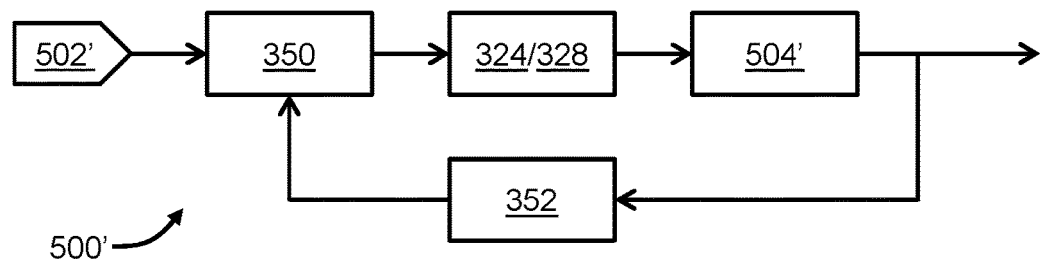

Similarly, referring to FIG. 5B, another exemplary embodiment of a control diagram 500' for a gas concentrating system, such as, for example, system 400', is illustrated. Control diagram 500' includes an initial set of control parameters 502' for controlling the pneumatic components of the system, control means 350, valving means 324 and/or valving means 328, sensing device or means 352, and the remaining gas concentrating system components 504' (e.g., system 400' less components 324, 328, 350, and 352). The initial set of control parameters 502' are read or input into control means 350. Control means 350 uses this initial parameter set to define the initial timing of the valving means 324 and/or valving means 328. Control means 350 also uses this initial parameter set 502' to define the timing of other components in block 504' (including the initial timing of the valving means 324 or valving means 328 if not already). Sensing device or means 352 senses the progress of the adsorption zone in the separation bed 310 (as represented by block 404') and communicates that information or data to control means 350. Control means 350 then uses the information from sensing device or means 352 to adjust the control parameters used by control means 350 in operating the gas concentrating system.

Figure 6A:
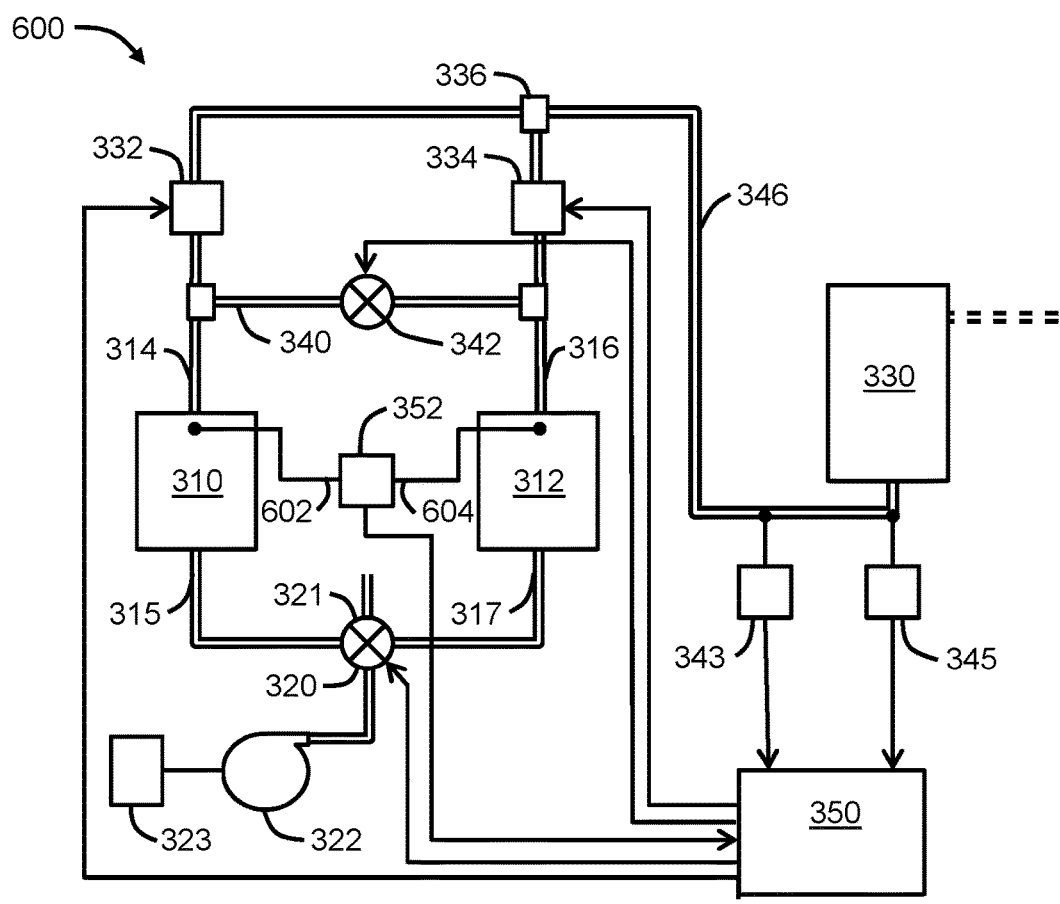
FIGS. 6A and 6B illustrate in schematic form two embodiments of gas concentrating systems with sensing devices associated with outlets of separation beds.
Figure 6B:
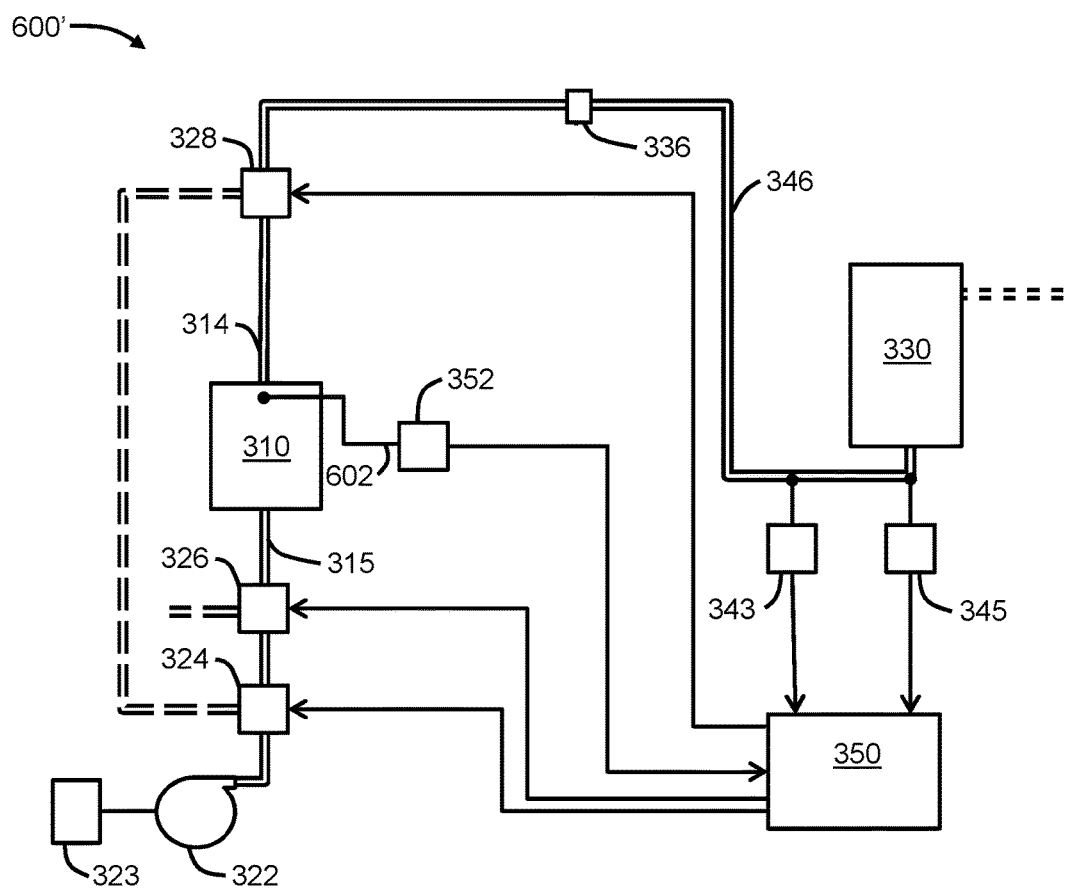

FIGS. 6A and 6B illustrate other embodiments of schematic diagrams of exemplary gas concentration systems 600, 600'. Systems 600, 600' are similar to systems 400, 400' of FIGS. 4A and 4B and illustrate a sensing device or means 352 to sense when the adsorption zone is approaching the separation bed outlet 314, 316. In one embodiment, the sensing device 352 is coupled to the inside of the separation bed 310, 312 near the separation bed outlet 314, 316 via lines 602, 604. In one embodiment, sensing device 352 can be connected to the upper portion of a side wall of a cylindrical separation sieve bed. In this manner, the sensing device 352 can identify when the breakthrough is approaching the separation bed outlet 314, 316. Control means 350 can control the various components associated with the fill and purge cycles of systems 600, 600' to prevent the breakthrough from reaching the separation bed outlets 314, 316. For example, this may allow for maximizing the fill cycle time while preventing the significant drop in the product gas oxygen concentration associated with breakthrough. The risk of breakthrough increases as the fill cycle time increases. In other words, the control means 350 can initiate switching from a fill cycle to a purge cycle right before breakthrough.

Figure 7A:
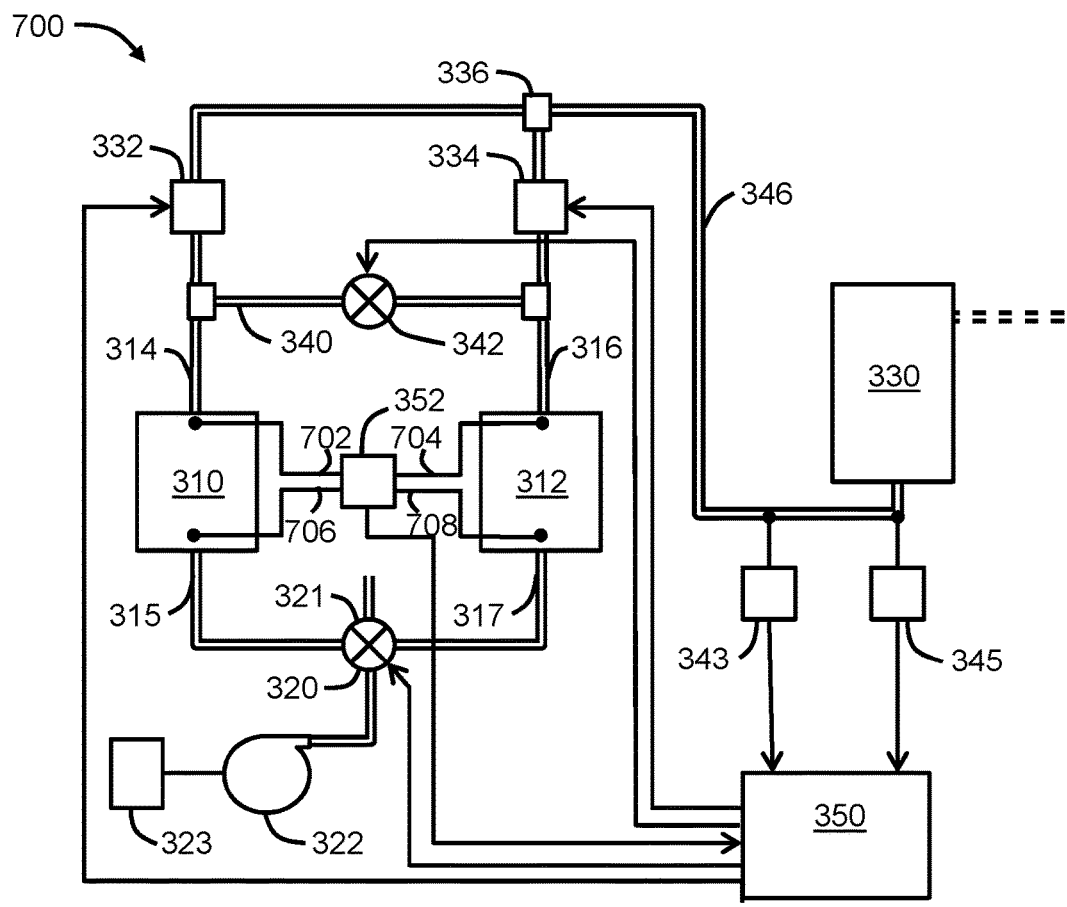
FIGS. 7A and 7B illustrate in schematic form two embodiments of gas concentrating systems with sensing devices associated with outlets and inlets of separation beds.
Figure 7B:
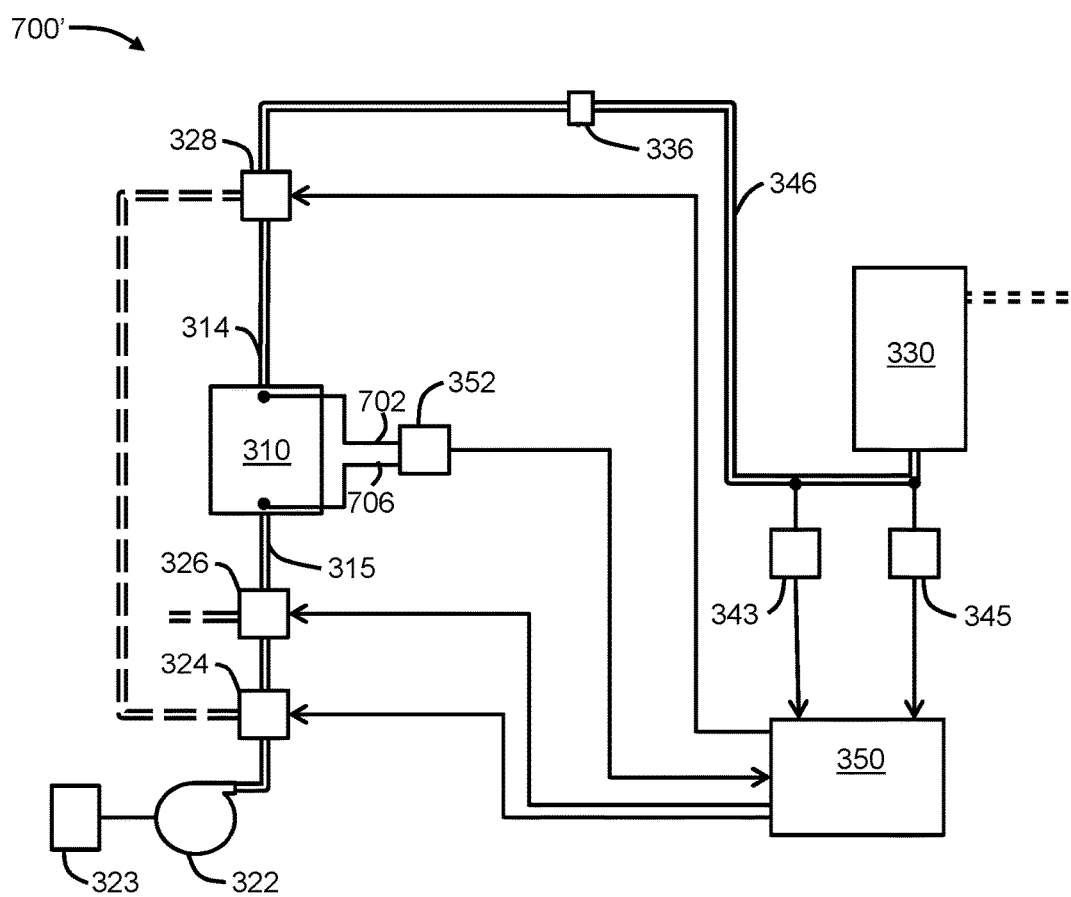

FIGS. 7A and 7B illustrate other embodiments of schematic diagrams of exemplary gas concentration systems 700, 700'. Systems 700, 700' are similar to systems 600, 600' of FIGS. 6A and 6B and illustrate a sensing device or means 352 that can additionally sense a characteristic of the separation bed 310, 312 near the separation bed inlet 315, 317 (e.g., oxygen concentration, nitrogen concentration, temperature, pressure, flow rate, etc.). In one embodiment, the sensing device 352 is coupled to the inside of the separation bed 310, 312 near the separation bed outlet 314, 316 via lines 702, 704 and additionally coupled to the inside of the separation bed 310, 312 near the separation bed inlet 315, 315 via lines 706, 708. In this embodiment, sensing device 352 can be connected to the upper and lower portions of a side wall of a cylindrical separation sieve bed.

In this manner, for example, the sensing device 352 can additionally identify when the adsorption zone is approaching the separation bed inlet 315, 317 during a purge cycle of the separation bed 310, 312. In particular, for example, when the nitrogen concentration level drops, for example, and compared to a particular predetermined threshold, the adsorption zone has returned to its unadsorbed size, the purging bed is considered purged, and is ready for the next fill cycle. Control means 350 can control the various components associated with the fill and purge cycles of systems 700, 700' to additionally optimize the purge cycle along with optimization of the fill cycle, as mentioned above. In other words, the control means 350 can initiate switching from a purge cycle to a fill cycle after a certain amount of desorption has occurred. In yet other embodiments, the sensing device can be connected portions between the upper and lower sections of a separation sieve bed.

As mentioned above, in this and other embodiments, appropriate control valving may be used to control from which location in the separation bed 310, 312 sensing device or means 352 is obtaining a reading, for example, from sensing paths 702, 704, 706, and 708. The control valving may be internal to sensing device or means 352 or may be in sensing paths 702, 704, 706, and 708.

Figure 8:
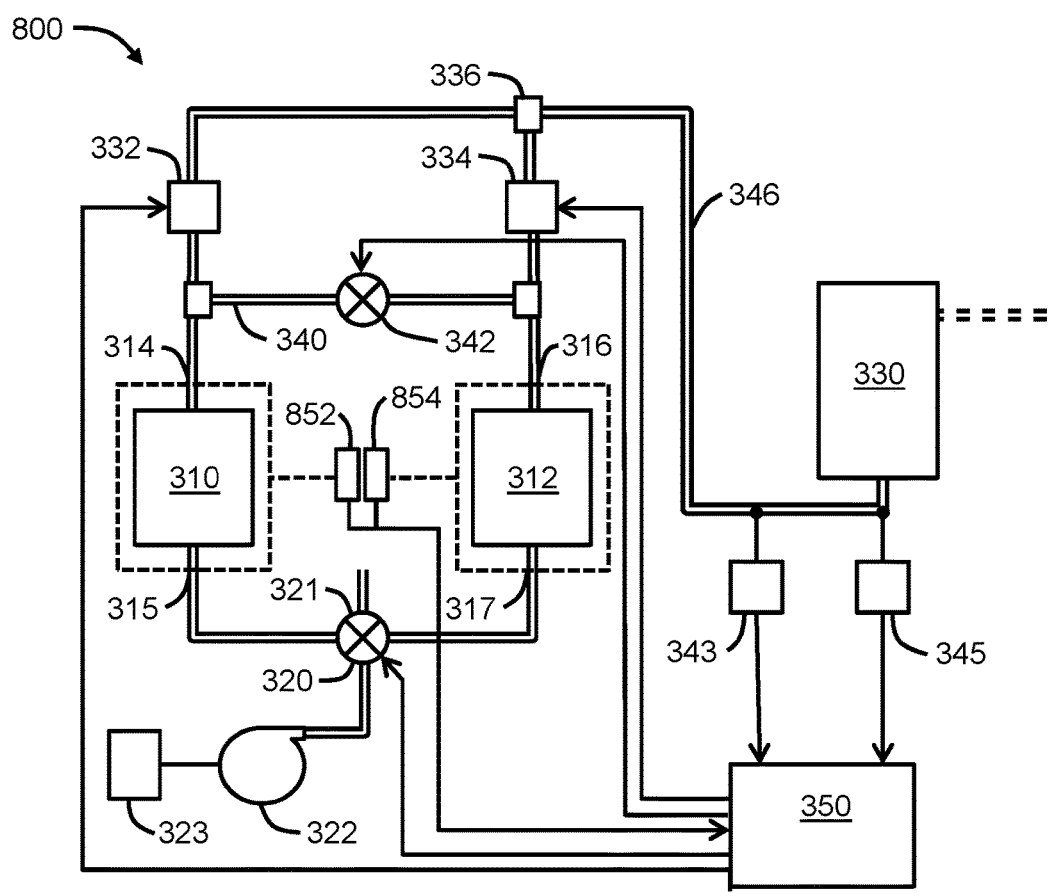
FIG. 8 illustrates in schematic form one embodiment of a gas concentrating system with two sensing devices associated with two separation beds.

FIG. 8 illustrates another exemplary embodiment of a schematic diagram of a gas concentrating system 800. System 800 is similar to system 300 and illustrates that sensing device or means 352 can, in one embodiment, include a sensing device 852 and 854 associated with each respective separation bed 310, 312. In this embodiment, control means 350 reads the sensing device 852, 854 that is associated with the respective separation bed 310, 312, during fill and/or purge cycles, depending on the location and parameter sensed. In additional embodiments, sensing device or means 352 can include any number of sensing devices integrated therein or as separate individual devices. Any other arrangement or configuration that provides control means 350 with the ability to sense parameters associated with the separation bed 310, 312, including, for example, the progress of an adsorption zone during a fill cycle, the progress of desorption during a purge cycle, combinations thereof, etc., can also be used.

Figure 9:
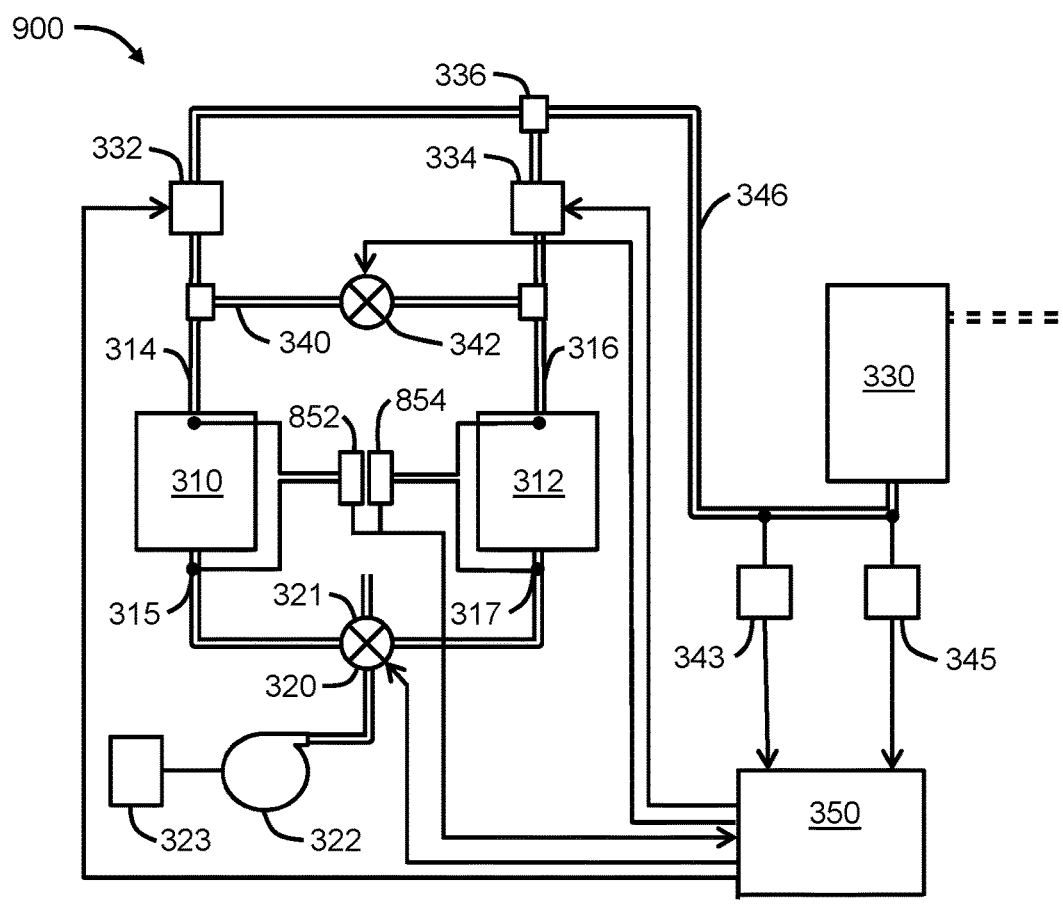
FIG. 9 illustrates in schematic form one embodiment of a gas concentrating system with two sensing devices associated with outlets and inlets of two separation beds.

Any of the above sensing devices or means 352 and their associated sensed locations may be combined in any number of various embodiments. For example, FIG. 9 shows another exemplary embodiment of a schematic diagram of a gas concentrating system 900. Similar to system 800 of FIG. 8, system 900 illustrates that sensing device or means 352 can, in one embodiment, include a sensing device 852 and 854 associated with each respective separation bed 310, 312. In addition, similar to system 700 of FIG. 7A, the sensing devices 852, 854 are each coupled to two sensed locations—one location associated with the top of the separation bed 310, 312 and another location associated with the bottom of the separation bed 310, 312. Similar to system 600 of FIG. 6A, for the top location, the sensing devices 852, 854 are each coupled to the inside of the separation bed 310, 312 near the separation bed outlet 314, 316. In addition, and not shown in the above systems, for the bottom location, the sensing devices 852, 854 are each coupled to a location outside of the separation bed 310, 312 near the separation bed inlet 315, 317. In addition, the sensing device(s) and sensed location(s) associated with one separation bed 310, 312 may be different than the sensing device(s) and sensed location(s) associated with another separation bed 310, 312 within the same gas concentrating system.

Figure 10:
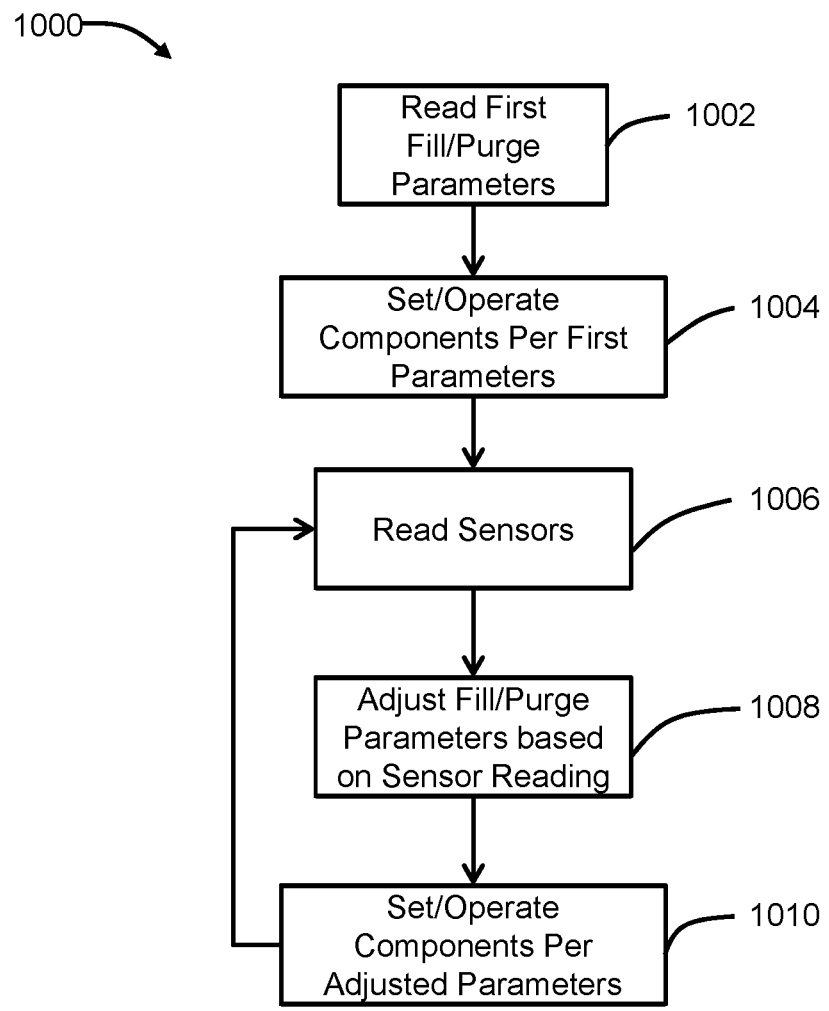
FIG. 10 illustrates a flow chart of one embodiment of a method to adjust a parameter set associated with a gas concentrating system.

Referring now to FIG. 10, one embodiment of a exemplary process flow chart 1000 for a gas concentrating system is illustrated. The rectangular elements denote processing blocks and represent computer software instructions or groups of instructions. The flow diagram(s) shown and described herein do not depict syntax of any particular programming language. Rather, the flow diagram(s) illustrate the functional information that may be used to fabricate circuits or to generate computer software to perform the processing of the system. It should be noted that many routine program elements, such as initialization of loops and variables and the use of temporary variables are not shown. Furthermore, the exact order of the process steps need not necessarily be performed in the order shown or described herein and may be modified.

In block 1002, control logic can read a first set of parameters associated with the control of the gas concentrating system. These parameters can be read, for example, from a memory associated with control means 350. The parameters can include, for example, all the operational settings for the pneumatic and other components of the gas concentrating system, such as, for example, in a two-bed gas concentrating system, crossover valving means 320, equalization device 342, and other controllable devices, such as motors and valves. The data may include timing, sequence, pressure, oxygen concentration, nitrogen concentration and other process or flow settings and subsets of the foregoing. In block 1004, the logic operates the components of the gas concentrating system according to the first set of parameters in order to produce concentrated gas product.

In block 1006, the sensing device or means 352 is read and input into control means 350. As described above, sensing device or means 352 provides information indicative of parameters associated with the separation bed 310, 312, including, for example, the progress of an adsorption zone during a fill cycle or the progress of desorption during a purge cycle. In one example, sensing device or means 352 is monitored to determine when the adsorption zone will reach the outlet 314, 316 or an area proximate to the outlet 314, 316 of a separation bed 310, 312. In this situation, sensing device or means 352 will indicate a change in its reading to indicate, for example, the adsorption zone has reached the outlet 314, 316 of the separation bed 310, 312, thereby producing a decrease in the oxygen concentration and/or increase in the nitrogen concentration measured at that outlet 314, 316. The timing of such an event is used in block 1008 to adjust one or more of the gas concentrating system control parameters, such as, for example, the opening and closing of equalization device 342. Other pneumatic and other components can also be adjusted, such as, for example, the timing of crossover valving means 320. Adjusting one or more of these parameters can result in a more efficient production of product gas from the system.

In block 1010, the adjusted control parameters are stored in memory and used to operate the system's pneumatic and other components according thereto. The logic then loops back to block 1006 to once again read the output of sensing device or means 352. As described above, the logic may loop back to block 1006 after each fill/purge cycle, or after a designated plurality of fill/purge cycles.

In this manner, the gas concentrating system can adjust its operating parameters, for example, based on the characteristics of actual absorption and desorption processes occurring in the separation beds, which may allow the system to account for various other factors affecting the effectiveness and/or efficiency of the absorption and desorption processes, including, for example, ambient temperature, ambient humidity, concentrations/content of source gas, etc. Other factors affecting the effectiveness and/or efficiency of the absorption and desorption processes may include, unanticipated flow impediments, including, for example, flow path obstructions, dirty filters, etc., moisture trapped in separation beds, exhaustion or contamination of separation material, leaking valves, weak pressure and/or vacuum sources, etc. Because these types of factors can affect the absorption and desorption processes, the adjusted parameter set may become quite different than the original parameter set, thereby maximizing the effectiveness, efficiency, etc., of the system in light of many possible conditions unanticipated by the original parameters. In some cases, the original parameter set may be based on ideal conditions, whereas the adjusted parameter set can account for non-ideal conditions. In these situations, the optimum performance of the system may not be possible, however, maximizing the effectiveness, efficiency, etc., of the non-ideal system may still be desirable.

The control or flow logic shown and described herein preferably resides in or on a computer readable medium such as, for example, a Read-Only Memory (ROM), Random-Access Memory (RAM), programmable read-only memory (PROM), electrically programmable read-only memory (EPROM), electrically erasable programmable read-only memory (EEPROM), magnetic disk or tape, and optically readable mediums including CD-ROM and DVD-ROM. Still further, the processes and logic described herein can be merged into one large process flow or divided into many sub-process flows. The order in which the process flows herein have been described is not critical and can be rearranged while still accomplishing the same results. Indeed, the process flows described herein may be rearranged, consolidated, and/or re-organized in their implementation as warranted or desired.

While the present invention has been illustrated by the description of embodiments thereof, and while the embodiments have been described in considerable detail, it is not the intention of the applicants to restrict or in any way limit the scope of the appended claims to such detail. Additional advantages and modifications will readily appear to those skilled in the art. For example, sensing including pressure, flow, and concentration (oxygen and/or nitrogen) can be employed to control the fill and purge cycle times. Furthermore, by using a elements such as, for example, micropumps, the entire gas concentrating system can be made smaller, quieter, more compact, having less vibration, and more efficient in terms of energy usage. The system can be powered by one or more batteries or other sources of mobile power. Furthermore, by integrating one or more of the components, modular assemblies can be made assisting in assembly, disassembly and repair of systems. Therefore, the invention, in its broader aspects, is not limited to the specific details, the representative apparatus, and illustrative examples shown and described. Accordingly, departures can be made from such details without departing from the spirit or scope of the applicants' general inventive concept.

The invention claimed is:
1. A system for producing a product gas, comprising:
a product gas separator, comprising a first separation bed to separate adsorbable components from a gas source;

at least one sensing device associated with the first separation bed to sense the progress of an adsorption zone within the first separation bed and provide an output;
a memory to store an original control parameter and an adjusted control parameter;
a controller, comprising logic to:
read the output of the at least one sensing device;
determine the adjusted control parameter based on the output of the at least one sensing device;
store the adjusted control parameter in the memory; and
control the separation of the adsorbable components from the gas source based on the stored control parameter, wherein the stored control parameter is based on non-ideal conditions occurring during separation of the adsorbable components.

2. The system of claim 1, wherein the controller further comprises logic to:
determine when an adsorption zone reaches or approaches an outlet of the first separation bed based at least in part on the output of the at least one sensing device;
wherein determining the adjusted control parameter is based on when the adsorption zone reaches or approaches the outlet of the first separation bed.

3. The system of claim 1, further comprising:
a second separation bed;
an equalization device connected to the first and second separation beds to selectively direct gas from one separation bed to the other separation bed;
wherein the controller further comprises logic to:
control the equalization device to selectively direct gas from one separation bed to the other separation bed based at least in part on the output of the at least one sensing device.

4. The system of claim 3, wherein the controller further comprises logic to:
determine when an adsorption zone reaches or approaches an outlet of the first or second separation bed based at least in part on the output of the at least one sensing device;
wherein controlling the equalization device includes selectively directing gas to the first or second separation bed when the adsorption zone reaches or approaches the outlet of the first or second separation beds.

5. The system of claim 1, wherein the controller further comprises logic to:
determine an average time for an adsorption zone to reach or approach an outlet of the first separation bed based at least in part on the output of the at least one sensing device;
wherein determining the adjusted control parameter is based on the average time for the adsorption zone to reach or approach the outlet of the first separation bed.

6. The system of claim 5, wherein the controller further comprises logic to:
determine a percentage of the average time for the adsorption zone to reach or approach the outlet of the first separation bed;
wherein determining the adjusted control parameter is based on the percentage of the average time for the adsorption zone to reach or approach the outlet of the first separation bed.

7. The system of claim 1, wherein the at least one sensing device associated with the first separation bed comprises at least one of a gas concentration sensor, a temperature sensor, a flow rate sensor, and a pressure sensor.

8. The system of claim 1, wherein the original control parameter is based on ideal conditions occurring during separation of the adsorbable components.

9. The system of claim 1, further comprising:
a second sensing device to sense the progress of desorption within the first separation bed and provide a second output;
wherein determining the adjusted control parameter is based on the second output of the second sensing device.

10. The system of claim 1, wherein controlling the separation of the adsorbable components from the gas source comprises triggering a valving means connected to the first separation bed to selectively direct gas from the gas source to the first separation bed.

11. The system of claim 1, wherein the non-ideal conditions occurring during production of the product gas comprise at least one of a temperature, a humidity, and a content of the source gas to the system.

12. The system of claim 1, wherein the non-ideal conditions occurring during production of the product gas comprise at least one of a flow impediment within the system, a reduced capacity of a separation bed material, a gas leak within the system, and a reduced capacity of a pressure source of the system.

13. A method of producing a product gas, comprising:
reading a first set of operating parameters;
reading an output of a first sensing device associated with the progress of an adsorption zone within at least one separation bed;
determining a second set of operating parameters based on the output of the first sensing device;
storing the second set of operating parameters in a memory; and
producing the product gas based on the stored set of operating parameters, wherein the stored set of operating parameters is based on non-ideal conditions occurring during production of the product gas.

14. The method of claim 13, further comprising:
determining when the adsorption zone reaches or approaches an outlet of the at least one separation bed based on the output of the first sensing device;
wherein determining the second set of operating parameters is based on when the adsorption zone reaches or approaches the outlet of the at least one separation bed.

15. The method of claim 13, further comprising:
determining an output volume rate for the product gas based on the output of a pressure sensor;
wherein determining the second set of operating parameters is based on the output volume rate for the product gas.

16. The method of claim 13, further comprising:
determining an average time for the adsorption zone to reach or approach an outlet of the at least one separation bed based on the output of the first sensing device;
wherein determining the second set of operating parameters is based on the average time for the adsorption zone to reach or approach the outlet of the at least one separation bed.

17. The method of claim 13, further comprising:
determining a percentage of the average time for the adsorption zone to reach or approach an outlet of the at least one separation bed;
wherein determining the second set of operating parameters is based on the percentage of the average time for the adsorption zone to reach or approach the outlet of the at least one separation bed.

18. The method of claim 13, further comprising:
reading an output of a second sensing device associated with the progress of a desorption zone within the at least one separation bed;
wherein determining the second set of operating parameters is based on the output of the second sensing device.

19. The method of claim 13, wherein the non-ideal conditions occurring during production of the product gas comprise at least one of a temperature, a humidity, and a content of a source gas.

20. The method of claim 13, wherein the non-ideal conditions occurring during production of the product gas comprise at least one of a flow impediment, a reduced capacity of a separation bed material, a gas leak, and a reduced capacity of a pressure source.

* * * * *